(12) United States Patent
Jain et al.

(10) Patent No.: US 11,740,208 B2
(45) Date of Patent: Aug. 29, 2023

(54) SWITCHED CAPACITOR DELAY LINE

(71) Applicant: TEXAS INSTRUMENTS INCORPORATED, Dallas, TX (US)

(72) Inventors: Prashuk Jain, Bengaluru (IN); Ravikumar Pattipaka, Bengaluru (IN); Vajeed Nimran Parambil Abdul Raheem, Bengaluru (IN); Sandeep Kesrimal Oswal, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 286 days.

(21) Appl. No.: 17/350,552

(22) Filed: Jun. 17, 2021

(65) Prior Publication Data
US 2021/0310996 A1 Oct. 7, 2021

Related U.S. Application Data

(63) Continuation of application No. 16/220,001, filed on Dec. 14, 2018.

(30) Foreign Application Priority Data

Oct. 31, 2018 (IN) .............................. 201841041182

(51) Int. Cl.
*G01S 7/52* (2006.01)
*G01N 29/24* (2006.01)
(Continued)

(52) U.S. Cl.
CPC ......... *G01N 29/2468* (2013.01); *G01N 29/36* (2013.01); *G01S 7/491* (2013.01);
(Continued)

(58) Field of Classification Search
None
See application file for complete search history.

(56) References Cited

U.S. PATENT DOCUMENTS 4,253,338 A 3/1981 Iinuma et al.
6,500,120 B1 12/2002 Anthony
(Continued)

OTHER PUBLICATIONS

Chen, Chao, et al. "A Front-End ASIC With Receive Sub-array Beamforming Integrated With a 32×32 PZT Matrix Fransducerfor 3-D Transesophageal Echocardiography", IEEE Journal of Solid-State Circuits, vol. 52, No. 4, Apr. 2017.

*Primary Examiner* — Hovhannes Baghdasaryan
(74) *Attorney, Agent, or Firm* — John R. Pessetto; Frank D. Cimino (57) ABSTRACT

A delay line control circuit includes a pseudo-random number generator and a random phase generator circuit coupled to the pseudo-random number generator. The pseudo-random number generator is configured to produce a predetermined sequence of pseudo-random values. The random phase generator circuit is configured to randomize an access sequence for capacitors of a delay line. The random phase generator circuit includes a sequence register, an adder, and gating circuitry. The sequence register is configured to a store a value identifying one of the capacitors to be accessed. The adder is coupled to the sequence register, and is configured to increment the value stored in sequence register. The gating circuitry is coupled to the pseudo-random number generator and the adder. The gating circuitry is configured to pass one of the pseudo-random values to the adder for addition to the value stored in the sequence register.

13 Claims, 5 Drawing Sheets

(51) Int. Cl.
    *G06F 7/58*          (2006.01)
    *G01S 7/491*       (2020.01)
    *G01N 29/36*     (2006.01)

(52) U.S. Cl.
    CPC ........ *G01S 7/5208* (2013.01); *G01S 7/52023* (2013.01); *G01S 7/52095* (2013.01); *G06F 7/582* (2013.01)

(56) References Cited

U.S. PATENT DOCUMENTS

| | | |
|---|---|---|
| 6,705,995 B1 | 3/2004 | Poland et al. |
| 9,351,706 B2 | 5/2016 | Rothberg et al. |
| 10,514,450 B2 | 12/2019 | Lee et al. |
| 10,613,205 B2 | 4/2020 | Mortensen et al. |
| 2010/0063399 A1 | 3/2010 | Walker et al. |
| 2015/0116695 A1 | 4/2015 | Bartolome et al. |
| 2016/0011305 A1 | 1/2016 | Koptenko |
| 2016/0363657 A1 | 12/2016 | Nakagawa et al. |
| 2017/0100096 A1 | 4/2017 | Min |

SWITCHED CAPACITOR DELAY LINE

CROSS-REFERENCE TO RELATED APPLICATIONS

This continuation application claims priority to U.S. patent application Ser. No. 16/220,001, filed Dec. 14, 2018, which claims priority to India Provisional Application No. 201841041182, filed Oct. 31, 2018, both of which are incorporated herein by reference in their entirety.

BACKGROUND

Beamforming is a signal processing technique used with sensor arrays for directional signal transmission or reception. Spatial selectivity is achieved by using adaptive or fixed receive/transmit beam patterns. Beamforming can be used for both electromagnetic waves (e.g., RF) and acoustic waves, and has found a variety of applications in radar, seismology, sonar, wireless communications, radio astronomy, speech, and medicine. Adaptive beamforming is used to detect and estimate the signal-of-interest at the output of a sensor array using data-adaptive spatial filtering and interference rejection.

Ultrasound imaging applications may use beamforming at the transmitter and/or the receiver. In ultrasound imaging applications, ultrasound energy may be focused at a target location by a transmit beamformer, and ultrasound energy modulated and returned from the target location may be focused by a receive beamformer. The receive beamformer may provide signals for generation of brightness (B-mode) images, and/or color Doppler or spectral Doppler information representing the target location, or combinations thereof. Beamforming is implemented with delay lines that align signals received at multiple ultrasound transducers for summation.

SUMMARY

A delay line control circuit that suppresses noise in a switched capacitor variable-delay circuit is disclosed herein. In one example, a delay circuit includes a plurality of sampling circuits and a control circuit. Each of the sampling circuits includes a sample capacitor, a sample switch, and a hold switch. The sample switch is coupled to the sample capacitor. The hold switch is coupled to the sample capacitor. The control circuit includes a pseudo-random number generator, and a random phase generator circuit coupled to the pseudo-random number generator and the sampling circuits. The random phase generator circuit includes a sequence register, an adder, and a plurality of sample control outputs. The adder includes a first input, a second input, and an output. The first input is coupled to an output of the pseudo-random number generator. The second input is coupled to an output of the sequence register. The output of the adder is coupled to an input of the sequence register. Each of the sample control outputs is coupled to a control input of the sample switch of one of the sample circuits.

In another example, a delay line control circuit includes a pseudo-random number generator and a random phase generator circuit coupled to the pseudo-random number generator. The random phase generator circuit includes a sequence register, and adder, and an encoding circuit. The adder includes a first input, a second input, and an output. The first input is coupled to an output of the pseudo-random number generator. The second input is coupled to an output of the sequence register. The output of the adder is coupled to an input of the sequence register. The encoding circuit includes an input and a plurality of outputs. The input is coupled to the output of the sequence register.

In a further example, a delay line control circuit includes a pseudo-random number generator and a random phase generator circuit coupled to the pseudo-random number generator. The pseudo-random number generator is configured to produce a predetermined sequence of pseudo-random values. The random phase generator circuit is configured to randomize an access sequence for capacitors of a delay line. The random phase generator circuit includes a sequence register, an adder, and gating circuitry. The sequence register is configured to a store a value identifying one of the capacitors to be accessed. The adder is coupled to the sequence register, and is configured to increment the value stored in sequence register. The gating circuitry is coupled to the pseudo-random number generator and the adder. The gating circuitry is configured to pass one of the pseudo-random values to the adder for addition to the value stored in the sequence register.

BRIEF DESCRIPTION OF THE DRAWINGS

For a detailed description of various examples, reference will now be made to the accompanying drawings in which.

DETAILED DESCRIPTION

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

Ultrasound probes include ultrasound transducers that convert acoustic signals to electrical signals. A variable delay line that includes multiple sampling capacitors and switching circuitry to switch signal to and from the capacitors is coupled to each of the ultrasound transducers to facilitate beamforming. If the sequence and timing of capacitor access in the delay line is invariant, then component parameter mismatch can create unwanted tones (i.e., spurs) in the delay line output signal. For example, mismatch in the parasitic capacitance or on resistance of the switches routing signal to and from each capacitor, or mismatch of the capacitors themselves may produce an error signal at the output of the delay line. The period of the error signal is a function of the capacitor access period. So, is if the capacitor access is periodic, then the error signal at the output of the delay line will be also be periodic, and may result in undesirable artifacts in an ultrasound image produced from the signal.

The delay circuits disclosed herein randomize the capacitor access sequence of a delay circuit to prevent the creation of unwanted tones in the delay circuit output signal. The capacitor access sequence is randomized by adding, at the start of each cycle through the capacitors, a pseudo-random value to a sequence value representing the next capacitor to be accessed. The randomized sequence is applied at both capacitor input and output. Some implementations of the delay circuit further randomize capacitor access by randomly changing the number of capacitors accessed in each cycle through the capacitors.

Figure 1:
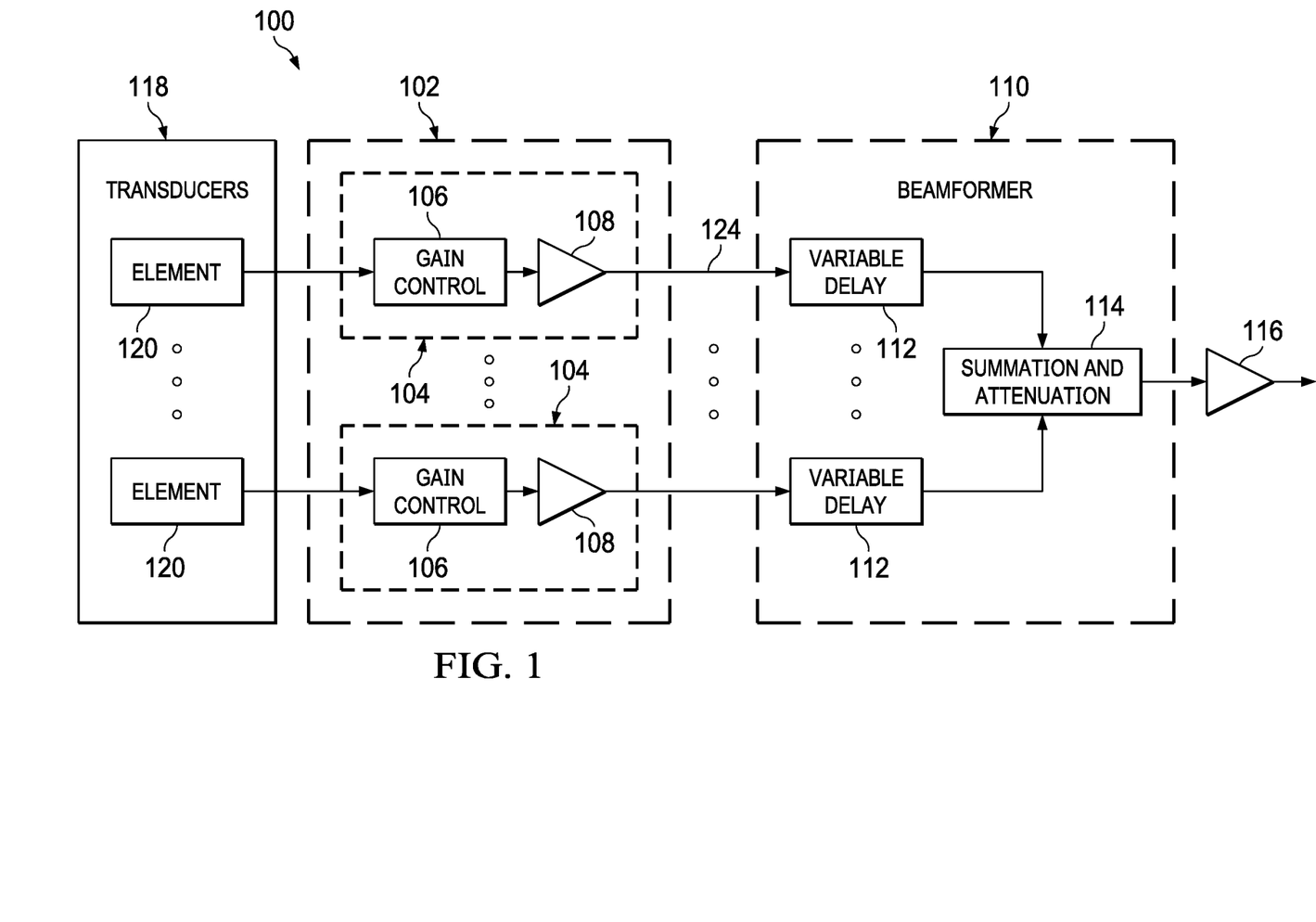
FIG. 1 shows a block diagram of an example receiver of an ultrasound probe in accordance with the present disclosure.

FIG. 1 shows a block diagram of the receiver 100 of an ultrasound probe in accordance with the present disclosure. The receiver 100 includes transducers 118, frontend circuitry 102, beamformer 110, and driver 116. The receiver 100 includes a large number (e.g., 2000, 3000, or more) of transducer elements 120 that convert acoustic energy into electrical signals. The transducer elements 120 are piezoelectric crystals, electro-magnetic transducers, MEMS transducers or other devices that converts sound waves into an electrical signal. The transducers 118 are coupled to the frontend circuitry 102.

The frontend circuitry 102 includes a number of channels 104. Each channel 104 is coupled to one of the transducer elements 120, and receives, from the transducer element 120, electrical signals representative of the acoustic signals incident on the transducer element 120. Each channel 104 includes an amplifier 108 (e.g., a low noise amplifier) and gain control circuitry 106. The gain control circuitry 106 adjusts the gain of the amplifier 108 and/or adjusts the amplitude of the electrical signal at the input of the amplifier 108 to optimize the amplitude of the signal provided to the beamformer 110. Some implementations of the gain control 106 include a digital time gain control circuit that varies the attenuation applied to the electrical signal and/or vary the gain of the amplifier 108 with time. The frontend circuitry 102 is coupled to the beamformer 110.

The beamformer 110 delays and sums signals 124 received from a number of channels 104 to produce an output signal with improved signal-to-noise ratio. The beamformer 110 includes variable delay circuitry 112, and summation and attenuation circuitry 114. While a single instance of the beamformer 110 is shown in FIG. 1, in practice the receiver 100 includes any number of beamformers 110 coupled to different combinations of the frontend channels 104. Each variable delay circuit 112 applies a programmable time delay to the signal received from a channel 104, where the time delay is selected to allow the output of the variable delay circuits 112 to be coherently summed in the summation and attenuation circuitry 114. For example, implementations of the beamformer 110 include 9, 12, 18, or other number of variable delay circuits 112, and the summation and attenuation circuitry 114 coherently sums the delayed signals and attenuates the signal summation. In some implementations, the number of channels 104 processed by the beamformer 110 is variable and set as needed.

The beamformer 110 is coupled to a driver 116. The driver 116 drives a cable connecting the receiver 100 to the other components of an ultrasound imaging system. The summation and attenuation circuitry 114 attenuates the signal output of the beamformer 110 to optimize the power of the driver 116, which drives the output of the receiver 100 onto a cable.

Figure 2:
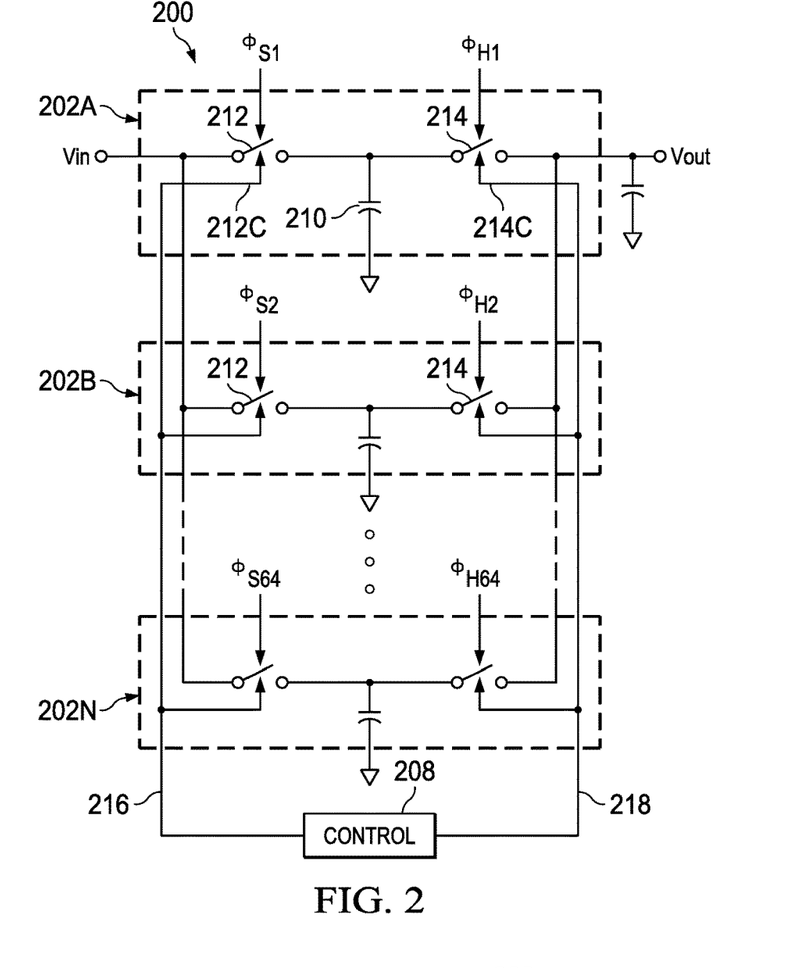
FIG. 2 shows a schematic level diagram for an example capacitor array included in a delay circuit in accordance with the present disclosure.

FIG. 2 shows a schematic level diagram for an example delay circuit 200 in accordance with the present disclosure. The delay circuit 200 is an implementation of the variable delay circuit 112. The delay circuit 200 includes a plurality of sampling circuits 202 (sampling circuit 202A, sampling circuit 202B, and sampling circuit 202N are shown) and a control circuit 208. The delay circuit 200 is illustrated as including 64 of the sampling circuits 202, but various implementations of the delay circuit 200 include any number of the sampling circuits 202. Each of the sampling circuits 202 includes a sample capacitor 210, a sample switch 212, and a hold switch 214. That sample switch 212 and the hold switch 214 are coupled to the sample capacitor 210. The sample switch 212 switchably couples the sample capacitor 210 to an input of the delay circuit 200, so that analog signal at the input of the delay circuit 200 charges the sample capacitor 210. The hold switch 214 switchably couples the sample capacitor 210 to an output of the delay circuit 200, so that the voltage across the sample capacitor 210, which represents a sample of the analog voltage at the input of the delay circuit 200, can be further processed (i.e., summed with output of multiple instances of the delay circuit 200).

The control circuit 208 is coupled to each delay circuit 200, and provides sampling control signals 216 and hold control signals 218 that individually control each sample switch 212 and each hold switch 214. Implementations of the control circuit 208 randomize the sequence in which the sample switches 212 are closed to sample the analog signal, and correspondingly randomize the sequence in which the hold switches 214 are closed to provide a delayed version of the analog signal. By randomizing the activation sequence of the sample switches 212 and the hold switches 214, the control circuit 208 reduces the incidence of undesirable tones in the output signal of the delay circuit 200. In some implementations, the control signals 216 are shared by multiple instances of the 200, and a different set of the control signals 218 is provided to each instance of the 200.

Figure 3:
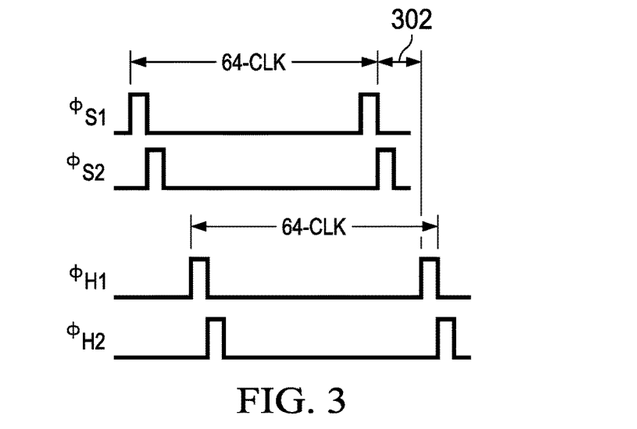
FIG. 3 shows an example of switch control signals applied to the capacitor array of FIG. 2.

FIG. 3 shows an example of switch control signals applied in the delay circuit 200. In FIG. 3, signal $\Phi_{S1}$ and signal $\Phi_{S2}$ are sampling control signals 216. While only signal $\Phi_{S1}$ and signal $\Phi_{S2}$ are shown in FIG. 2, the control circuit 208 generates a control signal for each sample switch 212. The signal $\Phi_{S1}$ controls closure of the sample switch 212 of the sampling circuit 202A and the signal $\Phi_{S2}$ controls closure of the sample switch 212 of the sampling circuit 202B. Closure of the sample switch 212 of the sampling circuit 202A by the signal $\Phi_{S1}$ charges the sample capacitor 210 of the sampling circuit 202A to the voltage at the input of the delay circuit 200, and closure of the sample switch 212 of the sampling circuit 202B by the signal $\Phi_{S2}$ charges the sample capacitor 210 of the sampling circuit 202B to the voltage at the input of the delay circuit 200.

In FIG. 3, signal $\Phi_{H1}$ and signal $\Phi_{H2}$ are hold control signals 218. While only signal $\Phi_{H1}$ and signal $\Phi_{H2}$ are shown in FIG. 2, the control circuit 208 generates a control signal for each hold switch 214. The signal $\Phi_{H1}$ controls closure of the hold switch 214 of the sampling circuit 202A and the signal $\Phi_{H2}$ controls closure of the hold switch 214 of the sampling circuit 202B. Closure of the hold switch 214 of the sampling circuit 202A by the signal $\Phi_{H1}$ provides the voltage across the sample capacitor 210 of the sampling circuit 202A at the output of the delay circuit 200, and closure of the hold switch 214 of the sampling circuit 202B by the signal $\Phi_{H2}$ provides the voltage across the sample capacitor 210 of the sampling circuit 202B at the output of the delay circuit 200. Thus, illustrated as interval 302, the signal at the output of the delay circuit 200 is delayed relative to the signal at the input of the delay circuit 200 by the time between deactivation of the signal $\Phi_{S1}$ and activation of the signal $\Phi_{H1}$.

Figure 4:
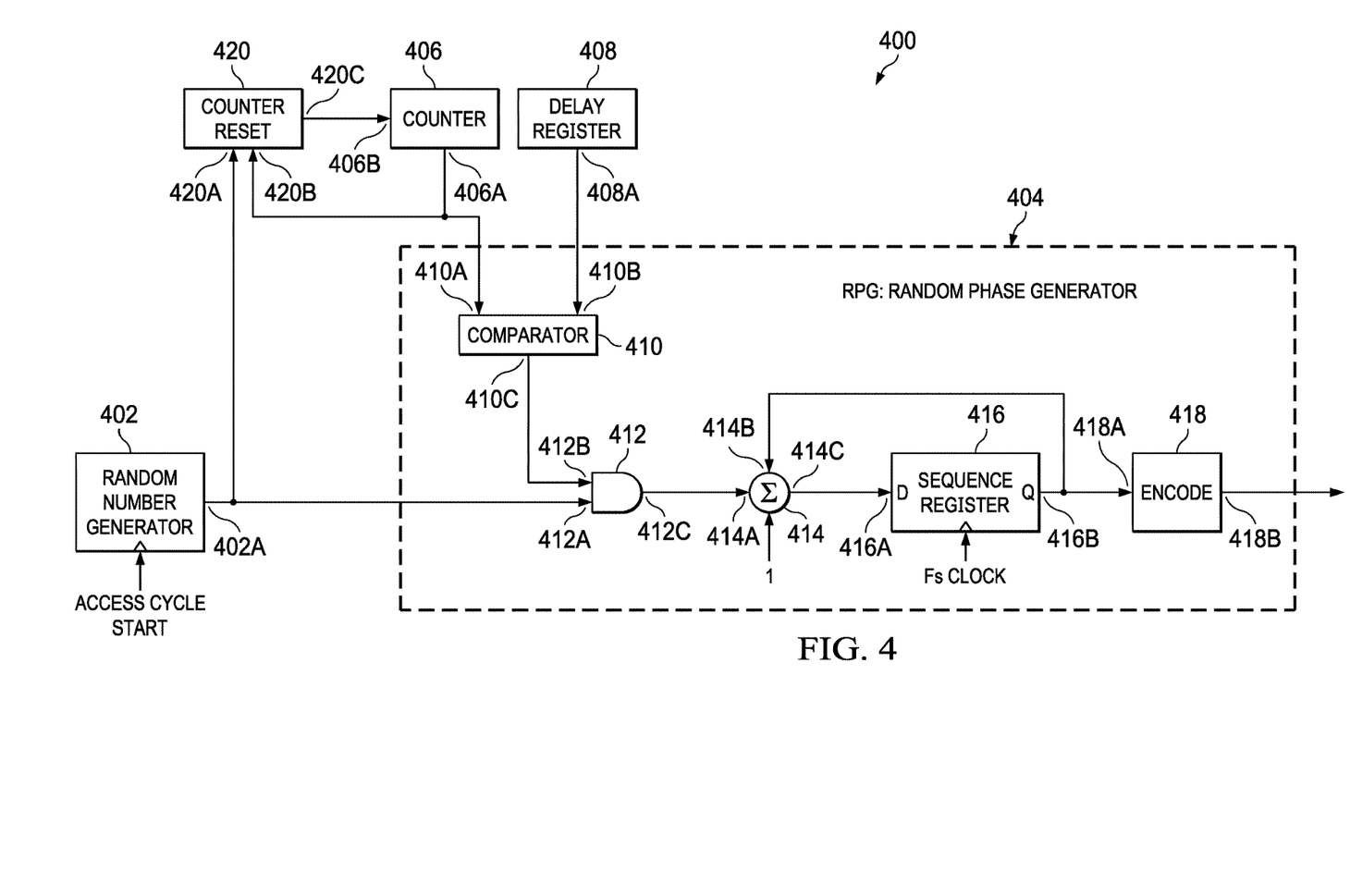
FIG. 4 shows a block diagram for an example delay line control circuit in accordance with the present disclosure.

FIG. 4 shows a block diagram for an example delay line control circuit 400 in accordance with the present disclosure. The delay line control circuit 400 is included in an implementation of the control circuit 208. The delay line control circuit 400 includes a pseudo-random number generator 402, a random phase generator circuit 404, a counter 406, and delay register 408. Some implementations of the delay line control circuit 400 also include a counter reset circuit 420. The pseudo-random number generator 402 generates pseudo-random values (a predetermined sequence of pseudo-random values) that are used by the random phase generator circuit 404 to randomize the access sequence applied to the sampling circuits 202. The pseudo-random number generator 402 generates a different pseudo-random value for each successive access cycle. For example, if the delay circuit 200 includes 64 instances of the sampling circuits 202, in some implementations an access cycle is performed over 64 clock cycles, where one clock cycle is the time during which one of the sample switches 212 is closed. In FIG. 4, the pseudo-random value provided by the pseudo-random number generator 402 is three bits in width. The width of the pseudo-random value is different in some implementations of the delay line control circuit 400. The pseudo-random number generator 402 is coupled to and provides the pseudo-random value to the random phase generator circuit 404.

The random phase generator circuit 404 includes a sequence register 416, an adder 414, gating circuitry 412, a comparator 410, and an encoder 418. The sequence register 416 stores a sequence value that identifies one of the sampling circuits 202 to be accessed (e.g., one of the sample switch 212 or the hold switch 214 to be closed). The sequence register 416 includes an output 416B that is coupled to an input 418A of the encoder 418 and an input 414B of the adder 414. The encoder 418 encodes the sequence value stored in the sequence register 416 to generate the sampling control signals 216 or the hold control signals 218. For example, in some implementations, the encoder 418 is a one-hot encoder that sets one of N output bits, wherein N is the number of the sampling circuits 202, to close a sample switch 212 based on the sequence value received from the sequence register 416. If the sequence value provided by the sequence register 416 is 6 bits in width, then the encoder 418 encodes the sequence value in a 64-bit field, where each bit represents one of the 64 different sequence values. Each of the sample control outputs 418B of the encoder 418 is coupled to a control input 212C of one of the sample switches 212, or to a control input 214C of one of the hold switches 214.

The adder 414 includes an output 414C that is coupled to the input 416A of the sequence register 416. The adder 414 updates the sequence value stored in the sequence register 416. In each clock cycle, where the sequence register 416 is clocked on each clock cycle, the adder 414 changes the sequence value stored in the sequence register 416. The adder 414 adds one to the current sequence value to select the next sampling circuit 202 to access. Thus, the delay line control circuit 400 generally sequentially accesses the sampling circuits 202. However, once per access cycle (e.g., once per 64 accesses), the adder 414 adds the pseudo-random value provided by the pseudo-random number generator 402 to the current sequence value, which causes a random change in the sampling circuit access sequence.

The gating circuitry 412, the comparator 410, the counter 406, and the delay register 408 select the time at which the pseudo-random value is added to the sequence value stored in the sequence register 416. The counter 406 counts the number of clock cycles in an access cycle. For example, in some implementations, the counter 406 is a six-bit binary counter to count the 64 clock cycles in which the 64 sampling circuits 202 of the delay circuit 200 are accessed. The delay register 408 stores a value that specifies the counter output value at which the pseudo-random value is added to the sequence value stored in the sequence register 416. For example, if the value stored in the delay register 408 is zero, then when the counter output value is zero (e.g., the first cycle of an access cycle), the pseudo-random value is added to the sequence value stored in the sequence register 416.

The comparator 410 compares the counter output value to the value stored in the delay register 408 to determine when the pseudo-random value is to be added to the sequence value stored in the sequence register 416. An input 410A of the comparator 410 is coupled to an output 406A of the counter 406, and input 4106 of the comparator 410 is coupled to an output 408A of the delay register 408. The gating circuitry 412 includes an input 412A that is coupled to an output 402A of the pseudo-random number generator 402, an input 412B that is coupled to an output 410C of the comparator 410, and an output 412C that is coupled to an input 414A of the adder 414. When the comparator 410 determines that the output value of the counter 406 is equal to the value stored in the delay register 408, the gating circuitry 412 passes the pseudo-random value provided by the pseudo-random number generator 402 to the adder 414 for addition to the value stored in the sequence register 416. Otherwise, the gating circuitry 412 passes zero to the adder 414. Thus, once per access cycle the sequence in which the sampling circuits 202 are accessed is randomly changed to prevent the introduction of unwanted tones in the output of the delay circuit 200.

In the implementation of the delay line control circuit 400 shown in FIG. 4, the sequence register 416 and the adder 414 are six bits in width to control 64 sampling circuits 202. The pseudo-random value provided by the pseudo-random number generator 402 is three bits in width. In the configuration of FIG. 4, the delay line control circuit 400 provides a delay of up to (62–7) 55 clock cycles. Other implementations of the 400, include a differently sized adder 414, sequence register 416, and pseudo-random value, and provide a different range of delay values.

Figure 5:
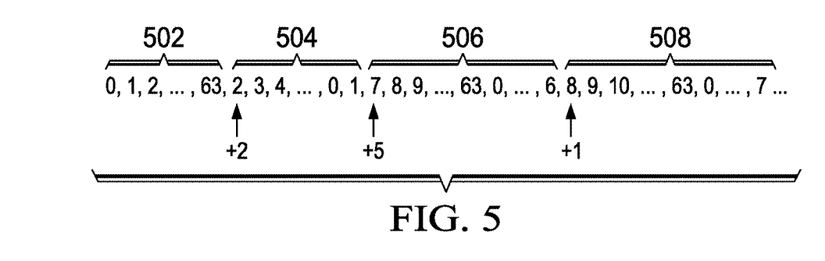
FIG. 5 shows an example of access cycles generated in the delay line control circuit of FIG. 4 in accordance with the present disclosure.

FIG. 5 shows an example of access cycles produced by the delay line control circuit 400. In FIG. 5, each access cycle is 64 clock cycles in length. Access cycle 502 begins with a sequence value of 0 and ends with a sequence value of 63. At the start of access cycle 504, the pseudo-random number generator 402 has generated a pseudo-random value of 2, and the adder 414 has added the 2 to the previous sequence value to produce a sequence value of 2. Thus, the access cycle 504 begins with a sequence value of 2 and rolls over to end with a sequence value of 1. At the start of access cycle 506, the pseudo-random number generator 402 has generated a pseudo-random value of 5, and the adder 414 has added the 5 to the previous sequence value to produce a sequence value of 7. Thus, the access cycle 506 begins with a sequence value of 7 and rolls over to end with a sequence value of 6. At the start of access cycle 508, the pseudo-random number generator 402 has generated a pseudo-random value of 1, and the adder 414 has added the 1 to the previous sequence value to produce a sequence value of 8. Thus, the access cycle 508 begins with a sequence value of 8 and rolls over to end with a sequence value of 7.

Figure 6:
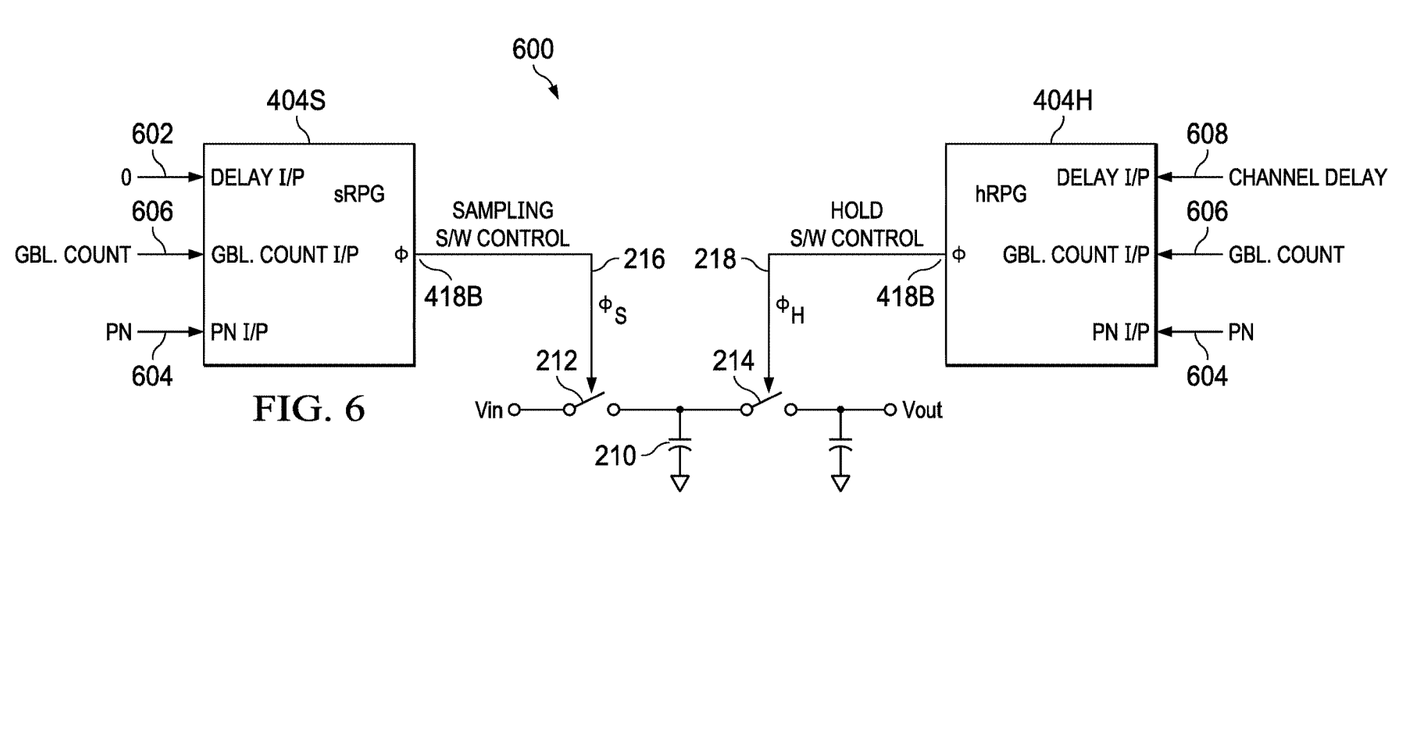
FIG. 6 shows a block diagram for an example delay circuit in accordance with the present disclosure

FIG. 6 shows a block diagram for an example delay circuit 600 in accordance with the present disclosure. In the delay circuit 600, a first instance of the random phase generator circuit 404 (labeled random phase generator circuit 404S) generates the sampling control signals 216 (provided at sample control outputs 418B of the 404S) for controlling the sample switches 212, and a second instance of the random phase generator circuit 404 (labeled random phase generator circuit 404H) generates the hold control signals 218 (provided at hold control outputs 418B of the 404H) for controlling the hold switches 214. Delay in the delay circuit 600 is controlled by the relative reset timing of the random phase generator circuit 404S and the random phase generator circuit 404H. In the delay circuit 600, the delay value 602 provided by the delay register 408 is set to zero, and the delay value 608 provided by a second instance of the delay register 408 is non-zero (e.g., 5 to produce a 4-cycle delay). Thus, in the random phase generator circuit 404S, the pseudo-random value 604 provided by the pseudo-random number generator 402 is added to the sequence value when counter output value 606 provided by the counter 406 is zero, and in the random phase generator circuit 404H, the pseudo-random value 604 provided by the pseudo-random number generator 402 is added to the sequence value when counter output value 606 provided by the counter 406 is five. Thereafter, with the five-cycle delay, the random phase generator circuit 404H generates the same sampling circuit access sequence as the random phase generator circuit random phase generator circuit 404S.

Figure 7:
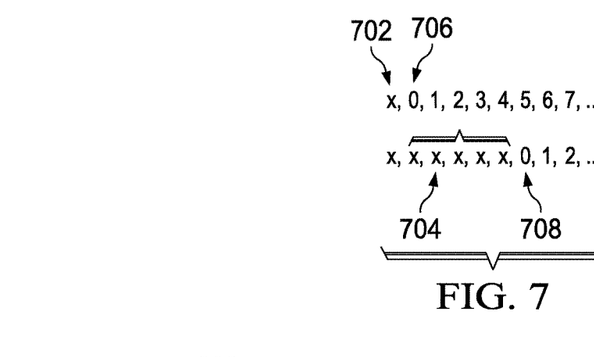
FIG. 7 shows example access sequences generated by delay line control circuits in accordance with the present disclosure.

FIG. 7 shows an access sequence 702 generated by the random phase generator circuit 404S and an access sequence 704 generated by the random phase generator circuit 404H. The delay value 602 is zero and the delay value 608 is five. The random phase generator circuit 404S starts to generate the sampling control signals 216 to access the sample switch 212 at cycle 706, and five cycles later, at cycle 708, the random phase generator circuit random phase generator circuit 404H starts to generate the hold control signals 218 to access the hold switch 214.

Returning now to FIG. 4, some implementations of the delay line control circuit 400 include the counter reset circuit 420 to further randomize the sampling circuit 202 access sequence by randomly changing the length of the access cycle. The counter reset circuit 420 selects a time to reset the counter 406 based on the output value of the counter 406 and the pseudo-random value provided by the pseudo-random number generator 402. Some implementations of the delay line control circuit 400 include two instances of the pseudo-random number generator 402, one instance of the pseudo-random number generator 402 provides a pseudo-random value to the random phase generator circuit 404, and another instance of the pseudo-random number generator 402 provides a pseudo-random value to the counter reset circuit 420. The counter reset circuit 420 includes a random value input 420A, a count value input 420B, and a reset output 420C. The random value input 420A is coupled to the output 402A of the pseudo-random number generator. The count value input 420B is coupled to the output 406A of the counter 406. The reset output 420C is coupled to a reset input 406B of the counter 406. The counter reset circuit 420 subtracts the pseudo-random value received from the pseudo-random number generator 402 from the value of the counter defining the end of an access cycle. For example, if the maximum access cycle length is 64 clock cycles, then the counter reset circuit 420 subtracts the pseudo-random value received from the pseudo-random number generator 402 from 64, and when the output value provided by the counter 406 is equal to 64 less the pseudo-random value, the counter reset circuit 420 resets the counter 406. Thus, operation of the counter 406 is made aperiodic, and the access cycles are aperiodic. In implementations that apply the counter reset circuit 402 to provide aperiodic operation of the counter 406, the reset signal provided at the reset output 420C of the counter reset circuit 402 is used to clock the pseudo-random number generator 402, thereby causing the pseudo-random number generator 402 to produce a new pseudo-random value at the start of each successive access cycle.

Figure 8:
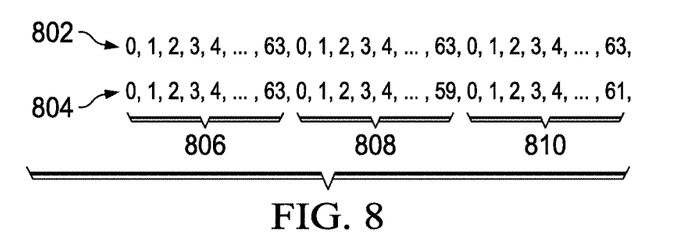
FIG. 8 shows count sequences generated with and without aperiodic reset in a delay line control circuit in accordance with the present disclosure.

FIG. 8 shows an example count sequence 802 generated by the counter 406 without aperiodic reset, and a count sequence 804 generated by the counter 406 with aperiodic reset by the counter reset circuit 420. In the count sequence 802 the counter '406 periodically counts from 0 to 63. In access cycle 806, the counter 406 counts from 0 to 63. In access cycle 808, the pseudo-random number generator 402 provides a pseudo-random value of 4, and the counter reset circuit 420 resets the counter 406 at cycle 59. In access cycle 810, the pseudo-random number generator 402 provides a pseudo-random value of 2, and the counter reset circuit 420 resets the counter 406 at cycle 61.

Figure 9:
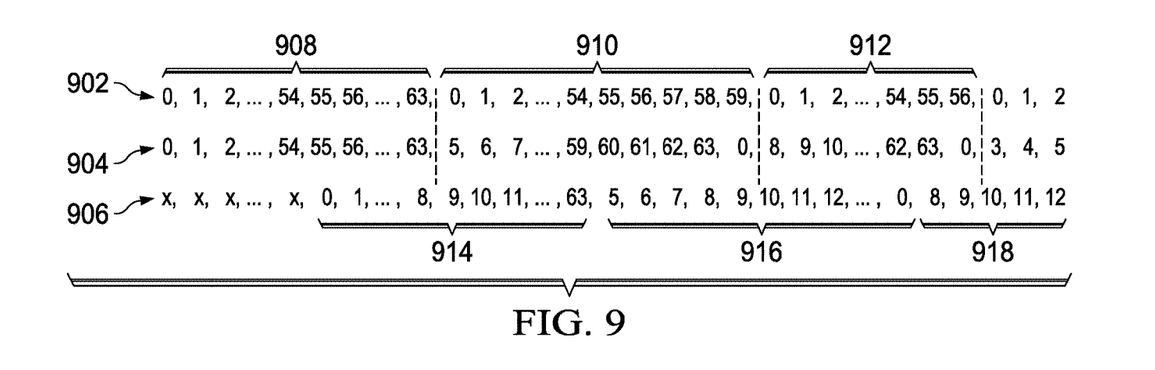
FIG. 9 shows example access sequences generated in a delay circuit in accordance with the present disclosure.

FIG. 9 shows an example of access sequences generated in the delay circuit 600. Sequence 902 is an aperiodic count sequence generated by the counter 406 with aperiodic reset by the counter reset circuit 420, sequence 904 is an output of the sequence register 416 of the random phase generator circuit 404S, and sequence 906 is an output of the sequence register 416 of the random phase generator circuit 404H. The delay value 602 provided to the random phase generator circuit 404S is zero, and the delay value 608 provided to the random phase generator circuit 404H is 55 to generate 54 cycles of delay. In the sequence 908, the counter 406 counts from 0 to 63, and the random phase generator circuit 404S generates an access sequence of 0 to 63. In the sequence 908, after a delay of 55 cycles, the random phase generator circuit 404H starts generation of an access sequence 914 of 0 to 63.

In the sequence 910, the counter 406 is aperiodically reset by the counter reset circuit 420 at cycle 59, and counts from 0 to 59. The pseudo-random number generator 402 provides a pseudo-random value of 5, which causes the random phase generator circuit 404S to generate an access sequence starting at 5 and rolling over to 0. The access sequence 914 generated by the random phase generator circuit 404H is complete at cycle 54 of the sequence 910. At cycle 55 of the sequence 910, the random phase generator circuit 404H applies the pseudo-random value of 5 to start an access cycle 916 at 5.

In the sequence 912, the counter 406 is aperiodically reset by the counter reset circuit 420 at cycle 56, and counts from 1 to 56. The pseudo-random number generator 402 provides a pseudo-random value of 7, which causes the random phase generator circuit 404S to generate an access sequence starting at 8 and rolling over to 0. The access sequence 916 generated by the random phase generator circuit 404H is complete at cycle 54 of the sequence 916. At cycle 55 of the sequence 916, the random phase generator circuit 404H applies the pseudo-random value of 7 to start an access cycle 918 at 8.

The above discussion is meant to be illustrative of the principles and various implementations of the present invention. Numerous variations and modifications will become apparent to those skilled in the art once the above disclosure is fully appreciated. It is intended that the following claims be interpreted to embrace all such variations and modifications.

What is claimed is:

1. A receiver of an ultrasound probe comprising:
    a plurality of transducers;
    frontend circuitry coupled to the plurality of transducers;
    a beamformer coupled to the frontend circuitry wherein the beamformer comprises:
    delay line control circuit, the delay line control circuit comprising:
    a pseudo-random number generator; and
    a random phase generator circuit coupled to the pseudo-random number generator, and comprising:
        a sequence register;
        an adder comprising:
            a first input coupled to an output of the pseudo-random number generator;
            a second input coupled to an output of the sequence register; and
            an output coupled to an input of the sequence register; and
        an encoding circuit comprising:
            an input coupled to the output of the sequence register; and
            a plurality of outputs.

2. The receiver of an ultrasound probe of claim 1, wherein the random phase generator circuit comprises gating circuitry comprising:
    a first input coupled to the output of the pseudo-random number generator; and
    an output coupled to the adder.

3. The receiver of an ultrasound probe of claim 2, wherein the random phase generator circuit comprises a comparator comprising an output coupled to a second input of the gating circuitry.

4. The receiver of an ultrasound probe of claim 3, further comprising:
    a counter comprising an output coupled to a first input of the comparator; and
    a delay register comprising an output coupled to a second input of the comparator.

5. The receiver of an ultrasound probe of claim 4, wherein the gating circuitry is configured to pass a value generated by the pseudo-random number generator to the adder responsive to a count value of the counter being equal to a value stored in the delay register.

6. The receiver of an ultrasound probe of claim 4, wherein the adder is configured to add one to a value stored in the sequence register based on the count value of the counter being not equal to a value stored in the delay register, and add a value generated by the pseudo-random number generator to the value stored in the sequence register based on the count value of the counter being equal to a value stored in the delay register.

7. The receiver of an ultrasound probe of claim 4, further comprising a counter reset circuit comprising:
    an input coupled to the output of the pseudo-random number generator; and
    an output coupled to a reset input of the counter.

8. The receiver of an ultrasound probe of claim 7, wherein the counter reset circuit is configured to reset the counter based on a value generated by the pseudo-random number generator.

9. A receiver of an ultrasound probe comprising:
    frontend circuitry;
    a beamformer coupled to the frontend circuitry wherein the beamformer comprises:
    delay line control circuit, the delay line control circuit comprising:
    a pseudo-random number generator configured to produce a predetermined sequence of pseudo-random values;
    a random phase generator circuit coupled to the pseudo-random number generator, the random phase generator circuit configured to randomize an access sequence for capacitors of a delay line, and comprising:
        a sequence register configured to a store a value identifying one of the capacitors to be accessed;
        an adder coupled to the sequence register, and configured to increment the value stored in the sequence register;
        gating circuitry coupled to the pseudo-random number generator and the adder, the gating circuitry configured to pass one of the pseudo-random values to the adder for addition to the value stored in the sequence register.

10. The receiver of an ultrasound probe of claim 9, wherein the random phase generator further comprises an encoding circuit coupled to the sequence register, and configured to activate a signal for accessing one of the capacitors based on the value stored in the sequence register.

11. The receiver of an ultrasound probe of claim 9, further comprising:
    a counter; and
    a delay register;
    wherein the random phase generator further comprises a comparator coupled to the counter, the delay register, and the gating circuitry; and the comparator is configured to activate the gating circuitry to pass the one of the pseudo-random values to the adder based on a value provided by the counter being equal to a value stored in the delay register.

12. The receiver of an ultrasound probe of claim 11, further comprising a counter reset circuit coupled to the counter and the pseudo-random number generator, and configured to reset the counter based on a value generated by the pseudo-random number generator.

13. The receiver of an ultrasound probe of claim 12, wherein the counter reset circuitry is configured to reset the counter based on the value provided by the counter being equal to a maximum value producible by the counter less the value generated by the pseudo-random number generator.

* * * * *